United States Patent [19]
Weinstein et al.

[11] Patent Number: 5,381,806
[45] Date of Patent: Jan. 17, 1995

[54] METHOD OF DELIVERING PRESSURE-INDUCED SENSATIONS

[75] Inventors: Sidney Weinstein, Lewisboro, N.Y.; Curt Weinstein, Danbury; Ronald Drozdenko, Woodbury, both of Conn.

[73] Assignee: Neurocommunication Research Laboratories, Inc., Danbury, Conn.

[21] Appl. No.: 166,206

[22] Filed: Dec. 13, 1993

Related U.S. Application Data

[60] Division of Ser. No. 978,109, Nov. 18, 1992, Pat. No. 5,316,011, which is a continuation-in-part of Ser. No. 860,900, Mar. 31, 1992, abandoned.

[51] Int. Cl.$^6$ .............................................. A61B 19/00
[52] U.S. Cl. .................................................... 128/744
[58] Field of Search ............... 128/740, 743, 744, 739, 128/741, 742, 774; 15/207.2

[56] References Cited

U.S. PATENT DOCUMENTS

| | | |
|---|---|---|
| 3,398,421 | 3/1967 | Rashbaum . |
| 3,633,235 | 1/1972 | Draca . |
| 3,662,744 | 5/1972 | Low . |
| 3,933,148 | 1/1976 | Wyler et al. . |
| 4,313,446 | 2/1982 | Kanatani . |
| 4,407,302 | 10/1983 | Hirshorn et al. . |
| 4,571,768 | 2/1986 | Kawashima . |
| 4,724,569 | 2/1988 | Eguchi et al. . |
| 4,958,402 | 9/1990 | Weinrauch . |
| 5,027,828 | 7/1991 | Kovacevic et al. . |
| 5,222,504 | 6/1993 | Solomon ........................ 128/744 |

FOREIGN PATENT DOCUMENTS

1641263A1  4/1991  U.S.S.R. .

OTHER PUBLICATIONS

Report entitled "Comparison of Three Antipruritics and a Vehicle" by Sidney Weinstein, Curt D. Weinstein and Ronald Drozdenko given at Alcon Laboratories, Inc., Apr. 29, 1980, pp. 1–8.

Article entitled "Pocket Filaments and Specifications for the Semmes–Weinstein Monofilaments" by Judith Bell-Krotiski, published in the Journal of Hand Therapy, Jan.–Mar., 1990, pp. 26–30.

*Primary Examiner*—Stephen C. Rellegrino
*Assistant Examiner*—Guy V. Tucker
*Attorney, Agent, or Firm*—Frishauf, Holtz, Goodman & Woodward

[57] ABSTRACT

A method of measuring the itch sensitivity of a skin surface of a subject patient comprises applying a unitarily formed elongated stimulating monofilament having a curved, textured stimulating tip at a free end thereof to contact the skin surface of the subject patient. The stimulating monofilament is dragged both distally and proximally across the skin surface, and a degree of itch rating of the subject patient is recorded. An apparatus for delivering such pressure-induced sensations to a subject skin surface includes a handle having a distal portion for applying a stimulus and a proximal portion grippable by a user. The apparatus further includes a plurality of heads coupled to the distal portion of the handle, and a plurality of elongated stimulating monofilaments of varying diameters each attached to a respective one of the plurality of heads for contacting the subject skin surface. Each of the heads is individually rotatable around a longitudinal axis of the handle, and the plurality of monofilaments are arranged such that a monofilament of greatest diameter is attached to a head coupled to the handle at a distalmost portion of the distal portion of the handle.

5 Claims, 6 Drawing Sheets

METHOD OF DELIVERING PRESSURE-INDUCED SENSATIONS

The present application is a divisional application of application Ser. No. 07/978,109, filed on Nov. 18, 1992, now U.S. Pat. No. 5,316,011, which was a continuation-in-part of application Ser. No. 07/860,900 filed on Mar. 31, 1992, now abandoned. The entire contents of application Ser. No. 07/860,900 are incorporated herein by reference.

BACKGROUND OF THE INVENTION

This invention relates to a method for measuring itch sensitivity consistently and accurately so that antipruritic products for alleviating itch can be evaluated. This invention further relates to an apparatus for the measurement of tactile sensation which includes multiple-head monofilaments configured to make the monofilaments readily accessible for rapid use while at the same time protecting the monofilaments from damage.

The Semmes-Weinstein Pressure Aesthesiometer is a well known device to measure tactile thresholds. It comprises a set of several plastic filaments of constant length with various diameters that apply differing maximal forces across the different filaments. Such a conventional esthesiometer is useful for the measurement of skin irritations, but due to the presence of sharp edges on the tips of the filaments, this conventional esthesiometer causes pain and twisting errors which reduce measuring accuracy and which preclude its application to various measurements including itch sensation.

A procedure for measuring itch sensation has been described by applicant Sidney Weinstein in a report to Alcon Laboratories entitled "Comparison of Three Antipruritics and A Vehicle", dated Apr. 29, 1980. Monofilaments are used to produce itch by means of dragging a specified monofilament across the skin at a 45 degree angle. The characteristic force and length of the specific monofilament cause it to produce a distinctive itch for a particular person, as people have different thresholds for itch. The force applied by the monofilament is determined basically by the physical dimensions of the monofilament; each monofilament as applied to the skin surface applies an increasing force as it is bent, but once bent, applies a characteristic calibrated force (within a percentage error). If increasing force is applied, the monofilament bends without applying additional downward force to the test site. If further force is applied, the monofilament eventually kinks destructively or the contacting surface unintentionally slips off the surface of the subject skin test site.

This known itch measurement procedure relied upon the then existing Semmes-Weinstein Pressure Aesthesiometer, which rendered the measurements very unreliable due to the problems of twisting, breaking and slipping of the monofilament, and moreover, because the inducing procedure scratched a subject skin surface so as to alleviate itch while trying to measure same. Therefore, this prior procedure did not allow for the precise determination of functional relationships between antipruritics.

The conventional filament kit having a number of individual monofilaments, moreover, is cumbersome to carry, time consuming to use, and prone to damage. Typically, a handle is provided to which filaments of various diameters can be permanently attached or removably attached, one-by-one, to perform testing. While in a "storage configuration" the filaments are safe from breakage but are inaccessible and difficult to use rapidly. A device having a handle which includes multiple heads for simultaneously holding multiple filaments has been proposed by Judith Bell-Krotoski in the *Journal of Hand Therapy*, "Pocket Filaments and Specifications for the Semmes-Weinstein Monofilaments" (January–March 1990). The Bell-Krotoski holder, however, exposes the filaments to damage and breakage during use and storage.

Application Ser. No. 07/860,900 discloses an esthesiometer having a stable, functional easy to manufacture tip which better engages the skin of a subject and which overcomes the problems of pain errors and twisting errors. The apparatus disclosed therein comprises a set of unitarily formed monofilaments whose tips are textured and curved. The unitary tip of the monofilaments disclosed in application Ser. No. 07/860,900 accordingly does not break or fall off, and due to its texture and curvature is accordingly capable of eliciting tactile pressure stimulations that are more consistently of the pressure type and that are more accurately recordable than the conventional esthesiometer, which elicits both pressure and pain stimulations randomly.

OBJECTS OF THE INVENTION

An object of the present invention is to provide an apparatus having curved and textured monofilaments as disclosed in application Ser. No. 07/860,900, and a method of using same, that is applicable to the accurate and consistent measurement of itch sensation.

A further object of the present invention is to provide an apparatus for the measurement of pressure sensation which includes multiple-head monofilaments configured to make the monofilaments readily accessible for rapid use while at the same time protecting the monofilaments from damage.

SUMMARY OF THE INVENTION

According to the present invention, a method of measuring the itch sensitivity of a skin surface of a subject patient comprises applying a unitarily formed elongated stimulating monofilament having a curved, textured stimulating tip at a free end thereof to contact the skin surface of the subject patient, and recording a degree of itch rating of the subject patient. After contacting the skin surface, the monofilament is preferably dragged both distally and proximally along the skin surface to produce the measurable itch sensation.

Still further according to the present invention, an apparatus for delivering pressure-induced sensations to a subject skin surface includes a handle having a distal portion for applying a stimulus and a proximal portion grippable by a user, a plurality of heads coupled to the distal portion of the handle, and a plurality of elongated stimulating monofilaments of varying diameters each attached to a respective one of the plurality of heads for contacting the subject skin surface. Each of the heads is individually rotatable around a longitudinal axis of the handle, and the plurality of monofilaments are arranged such that a monofilament of greatest diameter is attached to a head coupled to the handle at a distalmost portion of the distal portion of the handle.

DETAILED DESCRIPTION

Figure 1:
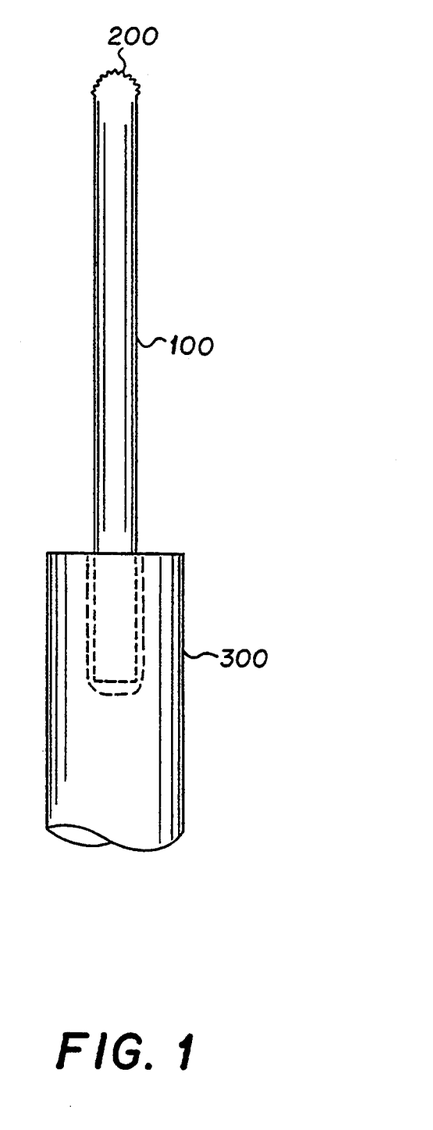
FIG. 1 illustrates the textured, curved stimulation tip of the present invention.

FIG. 1 shows the unitarily formed monofilament 100 of the present invention which has a textured, rounded stimulating tip 200 and which is embeddedly attached to a head 300.

The monofilaments of the present invention are made of nylon (such as Nylon 612 made by Du Pont) and have substantially the shape of a right cylinder. The force applied by each monofilament is determined by the physical parameters of diameter and length of each monofilament. The monofilaments all share a common length of approximately 38 mm and range in diameter from 0.0635 mm to 1.143 mm. These diameters correspond ascendingly to larger calibrated stimulus values, with larger diameter monofilaments delivering greater stimuli. The nominal values that are used to identify each monofilament are numbers that reflect the logarithm of the average force expressed in milligrams plus one; these numerals vary from 1.65 to 6.65. Each monofilament as applied to the surface of a subject skin test site applies an increasing force as it is bent, but once bent, it applies a characteristic calibrated force within a percentage error.

The stimulating tip of the monofilaments of the present invention are curved and textured. The advantage of the textured surface is that it makes unintentional slippage on the skin surface of the subject less likely, and the advantage of the curvature is that it functions to negate any twisting errors that occur by presenting essentially the same characteristic contacting face to the skin under conditions when the tip twists and when it doesn't twist. Thus, the stimulus provided by the monofilaments of the present invention is more constant and is consistently repeatable with a high degree of accuracy.

Accordingly, using the monofilament of the present invention having a curved textured stimulating top, high level touch stimulations do not appear as if they are pain level stimulations, as would occur in the conventional device if the filament twisted and an edge were presented to the examiner. Unintentional slippage causes an invalid stimulation level to be presented, twisting causes an edge instead of a flat face to be presented, and twisting errors are very common and not easily (if at all) controllable. The enhancement of the tip of the monofilaments of the present invention to solve these problems thus achieves great and unexpected advantages over conventional devices and over conventional attempts to attain a consistent stimulus.

Figure 2:
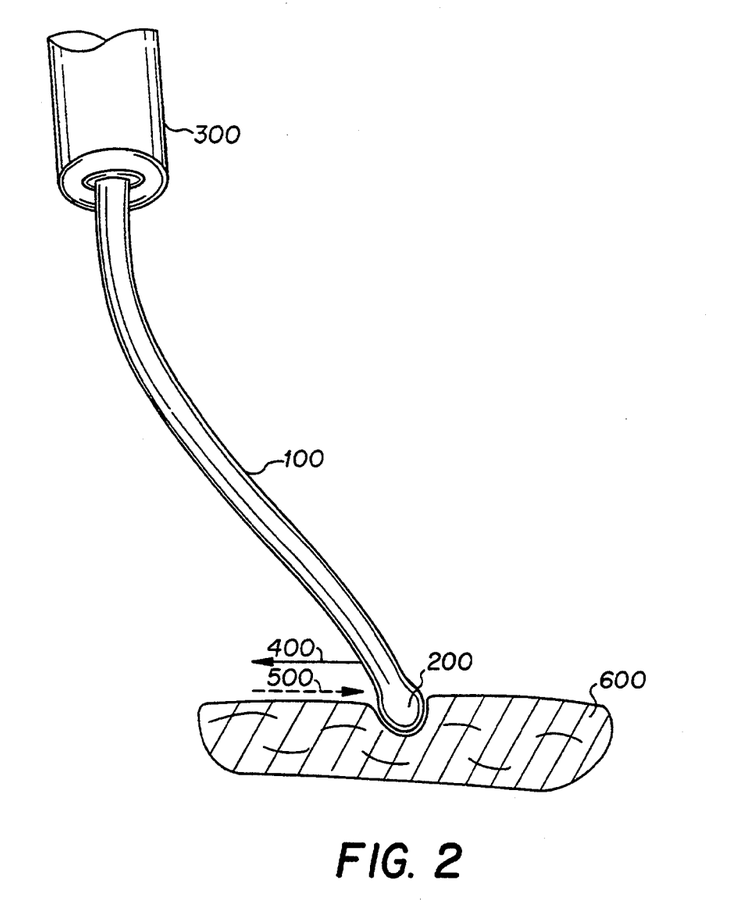
FIG. 2 illustrates the textured, curved stimulation tip applied to a subject skin surface according to the method of measuring itch sensation of the present invention.
Figure 2A:
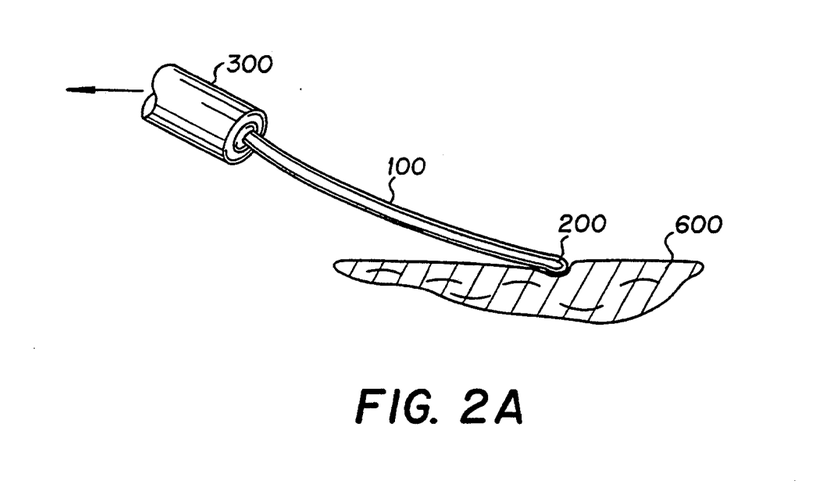
FIG. 2A shows another technique for applying the stimulation tip to a subject skin surface.

FIG. 2 shows a monofilament of the present invention applying its characteristic calibrated force, as operated according to the method of measurement of itch sensation of the present invention. Itch sensations are elicited by applying various nylon monofilaments at approximately a 45° angle to a subject skin surface and slowly dragging each monofilament across approximately 2-3 cm of the subject skin surface 600 in two opposite directions 400, 500, distally and proximally, the distal direction being toward the hand and the proximal direction being away from the hand. FIG. 2 shows dragging of the monofilament 100 in the direction of arrow 400. Pressure in a downward direction may be applied to slightly depress the skin of the patient at the area of contact with the monofilament. FIG. 2A shows another way to drag the monofilament 100 across the subject skin surface.

The 45° angle of application is a preferred angle, but other angles up to parallel with the skin are also effective, so long as the angle, once selected, is consistently maintained. The diameters of the various nylon monofilaments are, for example, approximately 0.1016 mm, 0.1524 mm, 0.2286 mm, 0.3048 mm, 0.3810 mm, 0.3810 mm, 0.4318 mm, and 0.5588 mm, as described in application Ser. No. 07/860,900.

Pre-itch and post-itch sensation thresholds are determined by either sequentially applying, one-by-one, a series of monofilaments of increasing diameter or decreasing diameter, depending on the subject number. For example, to test the antipruritic efficacy of a product, five monofilaments may each be used to deliver five stimulations at four sites, so that 100 (i.e., 5×5×4) stimulations will be delivered both prior to and following the application of the product.

The subject skin surface testing sites may be chosen on the basis of the distribution of peripheral cutaneous nerve. For example, to test a forearm, a point midway between the wrist an elbow may be designated the proximal boundary and the wrist the distal boundary. The ulnar and radial aspects can be further subdivided into four sites. The four sites are examined for apparent dermatological abnormalities, and are prepared prior to testing by clipping any long hairs in the areas and by swabbing with physiological saline in order to remove any residue from soap, lotion, etc.

Prior to data recording, a subject patient should preferably be familiarized with the procedure by several stimulations with each monofilament at each testing site, so that a basis may be formed for subsequent ratings. The subject patient receiving the stimulations rates the degree of itch produced by each stimulation on an eleven point scale between 0 and 10, with 0 representing "no itch" and 10 being "severe itch". When itch is reported, testing is suspended until itch sensation is no longer felt in order to avoid potential confusion with subsequent stimulations. All sites are tested with a same diameter monofilament before changing to the monofilament of next diameter, and the order of site tested is constant, progressing, for example from right radial to right ulnar to left ulnar to left radial.

In testing an antipruritic product, for example, itch sensations are measured both prior to application of the product to designated test sites, and, for example, five minutes following treatment with the product.

The subject patient's itch ratings are recorded and analyzed. A threshold monofilament is designated as the smallest diameter monofilament which produces itch. Pre-treatment and post-treatment data elicited by this threshold diameter are statically analyzed. The threshold filament is used as an itch index because monofilaments of smaller diameter do not elicit itch and because monofilaments of larger diameter are more likely to produce other sensations in addition to itch, such as pressure and abrasion. Statistical analysis of this data will yield an itch sensitivity measurement, and a determination as to the effectiveness of an antipruritic product. Various antipruritic products can be similarly and comparatively tested according to the same procedures.

Figure 3:
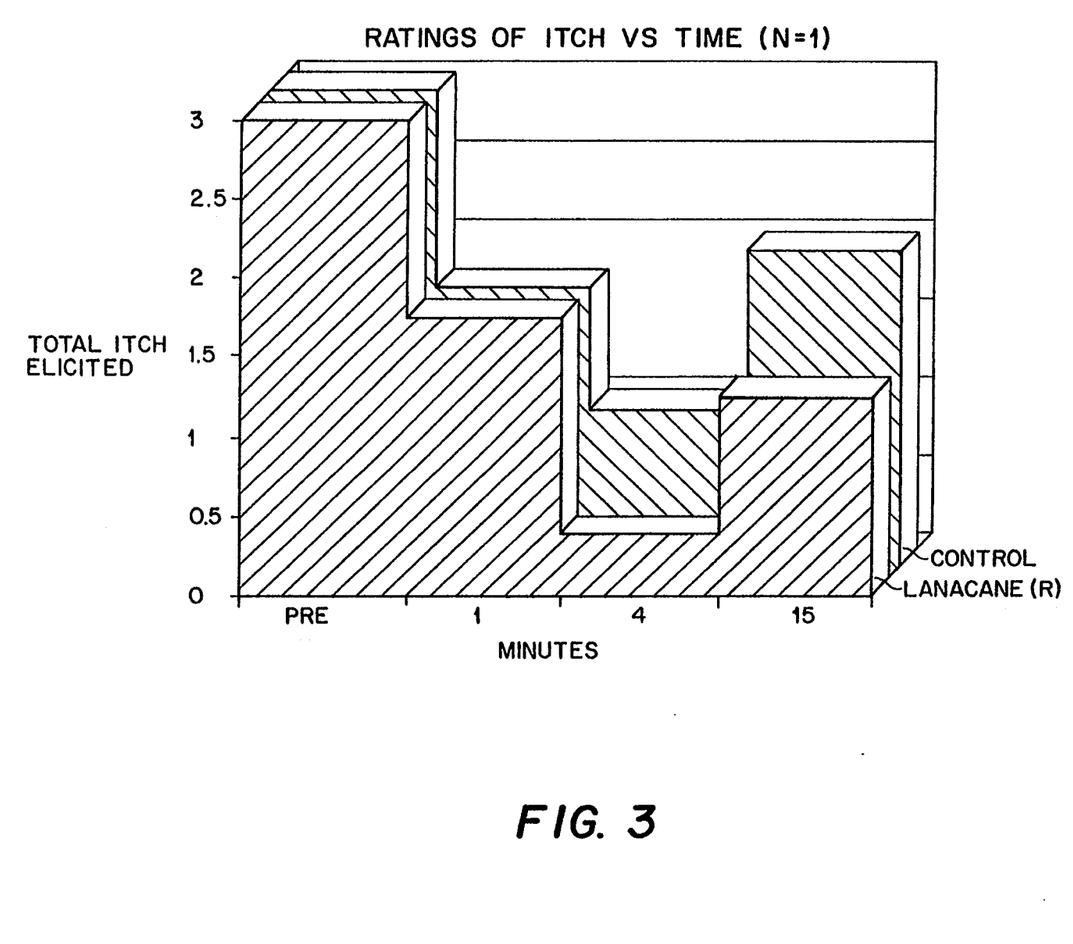
FIG. 3 illustrates the results of an itch sensitivity measurement performed according to the method of the present invention to test the effectiveness of a given antipruritic product.

FIG. 3 shows the results of an itch sensitivity measurement performed according to the method of the present invention to test the effectiveness of the antipruritic product Lanacane produced by Combe Corporation. A blinded subject patient was treated at test sites on the volar forearms with a vanishing cream (the control) and Lanacane (the active product). FIG. 3 shows that the amount of itch elicited prior to application (PRE) was exactly equal for both sites. At a time period of one minute after application, the lubricating and cooling effects of both the control and active product similarly reduced the elicited itch. At a time period of four minutes after application, the active product revealed an advantage in reducing itch, and this advantage of the active product over the control was still maintained at fifteen minutes after application.

Given the variability of subject patients, it is estimated that from 20 to 30 random subjects would most accurately evidence a statistically significant effect.

Thus, due to the uniquely configured curved and textured tip of the stimulating monofilament of the present invention which does not scratch the surface of the skin as the stimulating monofilament is dragged therealong, according to the above described method of the present invention, itch sensitivity and the effect of an antipruritic product is consistently and accurately measured.

Figure 4:
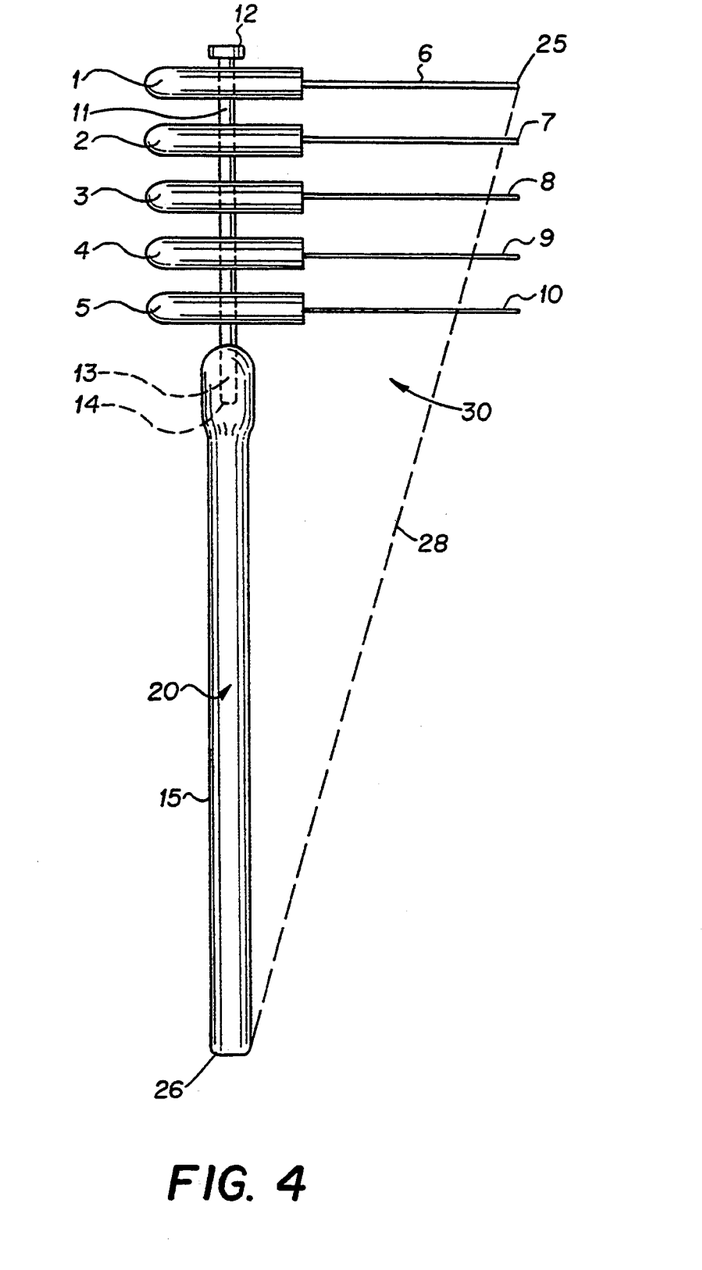
FIG. 4 illustrates an apparatus of the present invention having multiple-head monofilaments.

FIG. 4 shows an apparatus of the present invention having multiple-head monofilaments for performing pressure sensitivity measurements, such as in the original Semmes-Weinstein technique as well as according to the itch sensitivity measuring method described above. The multiple-head device of the present invention has application to the screening of peripheral nerves, as the original Semmes-Weinstein is employed, and toward this end, neurologists and hand surgeons could potentially employ the instrument for its calibrated stimuli in pressure in order to detect peripheral nerve impairment, determine the spatial extent of impairment and determine the degree of impairment. Applications thus would include screening for suspected cases of repetitive-motion nerve syndrome, screening for peripheral nerve diseases such as leprosy, gaining diagnostic information such as required in managing a diabetic limb, and determining the extent of sensory impairment due to lacerations or compression diseases. Researchers and product developers can also use the device to measure itch.

As shown in FIG. 4, a handle 20 comprises a proximal grippable portion 15 and a distal portion 11 carrying heads 1-5 which carry respective monofilaments 6-10. The handle 20 is grippable by a user at the proximal portion 15. The distal portion comprises a screw member 11 to which multiple monofilament heads 1-5 are rotatably coupled. A tip 13 of said screw member 11 is inserted within a recess 14 at the end portion of the proximal portion 15 of said handle 20. The heads 1-5 are rotatable on said screw member 11 around a longitudinal axis of said handle 20. Monofilaments 6-10 are each attached respectively to heads 1-5 so as to extend substantially perpendicularly from said handle 20. The heads 1-5 are positioned such that the monofilament 6 of greatest diameter is at a distalmost portion 12 of said screw member 11, and such that monofilaments 7-10 are positioned sequentially in order of decreasing diameter with the monofilament 10 of least diameter being at a proximalmost portion of said screw member 11.

The monofilaments 6-10 are shielded from damage and breakage within a protection zone 30. As shown in FIG. 4, the protection zone 30 is triangular in shape and is defined on its three sides by the longitudinal axis of the handle 20, the distalmost head 1 and its monofilament 6 of greatest diameter, and the dashed line 28 extending from the proximalmost end 26 of the handle 20 to the free end 25 of the monofilament 6 of greatest diameter. The handle 20, head 1 and monofilament 6 of greatest diameter are of such a strength as to absorb the impact of a typical shock against a hard surface without breakage or substantial bending. Thus, in a case where the device is dropped or inadvertently bumped, the monofilaments 7-10 bend only up to the vicinity of the dashed line 28, but do not break as they would otherwise in the absence of the distalmost positioning of the monofilament 6 of greatest diameter.

In a preferred embodiment, the monofilaments have the following approximate characteristics:

| Monofilament | Diameter | Calibrated Force | Sensation |
| --- | --- | --- | --- |
| 6 | 0.127 mm | 0.07 (g) | Normal |
| 7 | 0.1778 mm | 0.2 (g) | Diminished |
| 8 | 0.3048 mm | 2.0 (g) | Reduced protective |
| 9 | 0.3556/0.4318 mm | 4.0/10.0 (g) | Loss of protective |
| 10 | 1.016 mm | 200 (g) | Residual |

Figure 5:
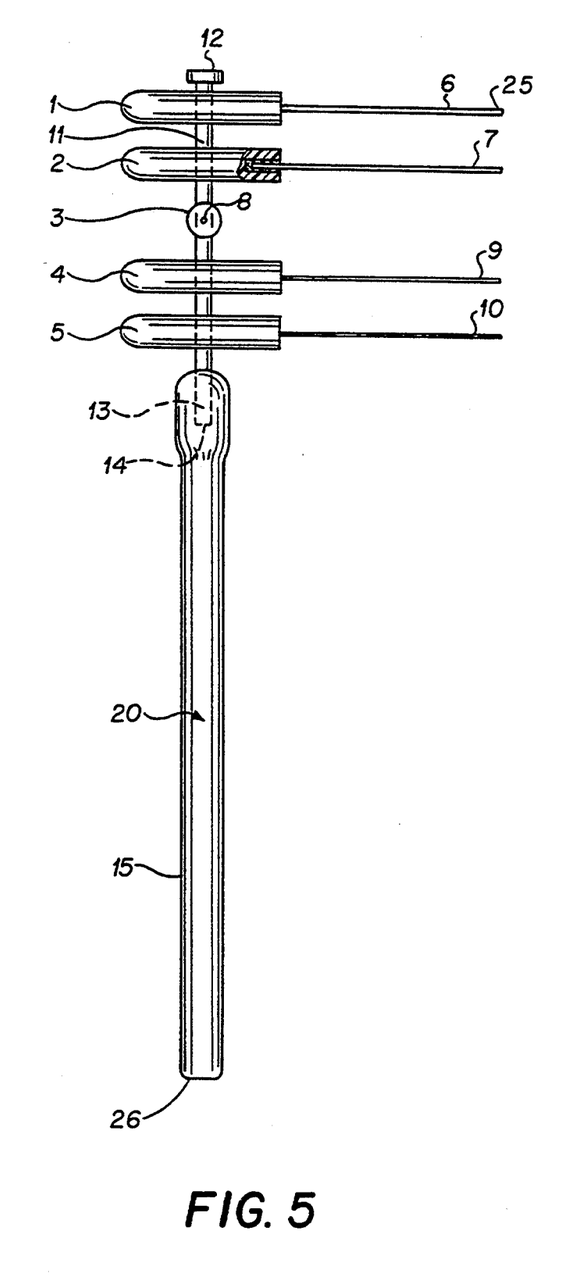
FIG. 5 illustrates the multiple-head monofilament apparatus of the present invention with one of said monofilament heads rotated to an operative position for application to a subject skin surface.

FIG. 5 illustrates the multiple-head monofilament apparatus of the present invention with one of said monofilament heads rotated to an operative position for application to a subject skin surface. Head 3 is individually rotated relative to the heads 1-2 and 4-5 approximately 90° around the longitudinal axis of the screw 11 into the operative position. In such operative position, monofilament 8 of head 3 is individually applicable to a subject skin surface for delivering pressure-induced sensation thereto. To measure pressure sensitivity, the monofilaments are applied perpendicular to the skin, whereas for itch production, the monofilaments are applied at approximately a 45° angle to the skin and dragged therealong.

Each of said heads 1-2 and 4-5 is similarly individually rotatable relative to the other heads to place respective stimulating monofilaments 6-7 and 9-10 of varying diameters, individually, in operative positions so that a range of pressure-induced sensations may be sequentially delivered to the subject skin surface. The present invention accordingly provides a simply configured multiple-head monofilament apparatus whose monofilaments are readily accessible for rapid and convenient use, and are at the same time protected from damage and breakage.

The monofilaments 6-10 are preferably mounted to the respective heads 1-5 by having their respective fixed ends embedded in a hollow end portion of a head and fixed thereto by means of an adhesive or by melted plastic, for example, as shown with respect to head 2 in FIG. 5.

The heads 1–5 are preferably made of plastic material which is easily moldable and are press fit or tightly fit over screw member 11 or another elongated member so that when twisted (for example, as shown in FIG. 5), they retain their position (by frictional engagement) against forces applied thereto while dragging along the skin. The distal portion 15 is also preferably made of plastic or metallic material.

Various alterations and modifications can be made, as should be apparent. For example, the elongated screw 11 may be an unthreaded shaft which has the heads 1–5 frictionally mounted thereon for rotation relative to the elongated member, the friction therebetween maintaining the head in a rotated position. In such a case, the end portion 13 of the elongated member (replacing screw 11) may be threaded to be engaged in a recess 14 of proximal portion 15 of the handle, or the end portion 13 may be unthreaded or otherwise press fit into an opening 14, or may be adhered by means of an adhesive such as epoxy.

The illustrated embodiments show five heads 1–5 with respective monofilaments 6–10 attached thereto. Any number of heads, however, can be used.

Figure 6:
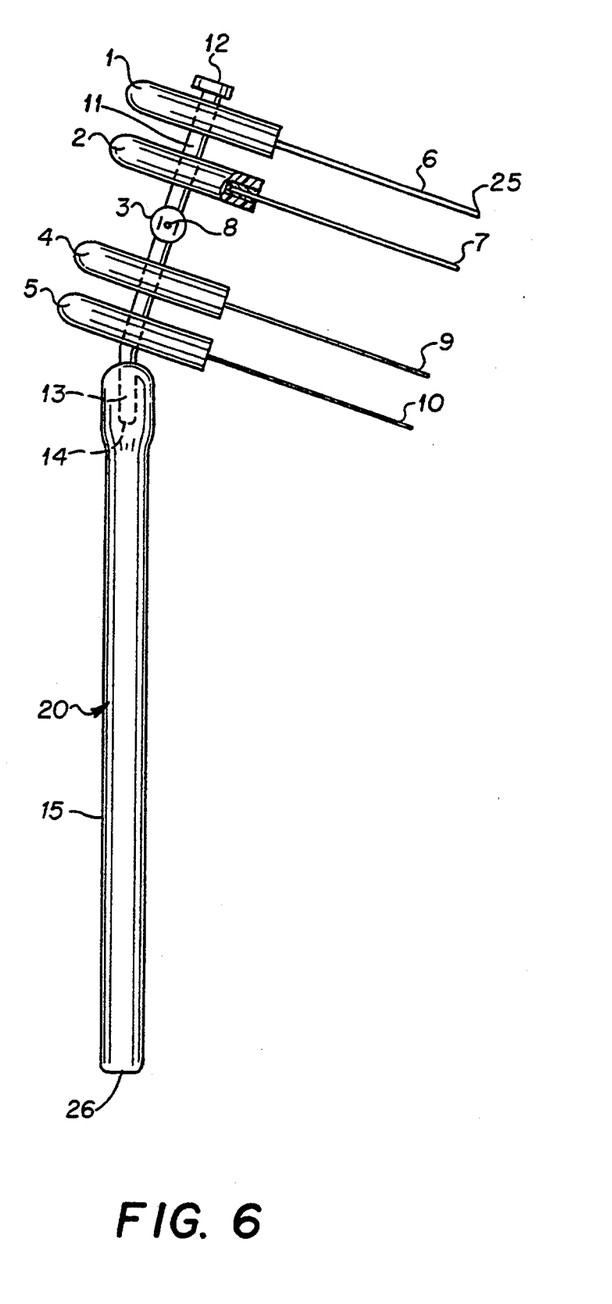
FIG. 6 illustrates a modification of the apparatus of FIG. 3.

Still further, while FIGS. 4 and 5 show the axis of the elongated screw 11 aligned with the axis of the proximal portion 15 of the handle, the axis need not be aligned as shown. For example, the axis of screw 11 can be offset relative to the axis of proximal portion 15 (and be substantially parallel with each other), or the axis of the elongated screw member may be at an angle relative to the axis of the proximal portion 15, as shown by way of example in FIG. 6.

The scope of the present invention is not intended to be limited to the embodiments particularly shown in the drawings and described above in the specification. It will be obvious to those skilled in the art that further various changes may be made without departing from the spirit and scope of the present invention as defined by the following claims.

What is claimed is:

1. A method of measuring an itch sensitivity of a skin surface of a subject patient, comprising:

contacting a unitarily formed elongated stimulating monofilament having a curved, textured stimulating tip at a free end thereof with said skin surface of said subject patient such that said stimulating tip contacts said skin surface; and wherein each of a plurality of stimulating monofilaments of varying diameters is attached to one of a plurality of heads of a stimulating device, each of said plurality of heads being individually rotatable relative to one another into an operative position, and wherein said step of contacting a stimulating monofilament comprises:

rotating one of said plurality of heads into said operative position such that said stimulating monofilament attached thereto is individually operable; and contacting said individually operable stimulating monofilament to said skin surface of said subject patient with increasing force until said individually operable stimulating monofilament bends at an acute angle to said skin surface;

dragging said individually operable stimulating monofilament across said skin surface over at least a given distance while said stimulating tip is in contact with said skin surface; and recording a degree of itch rating of said subject patient responsive to a patient reaction to said step of dragging of said stimulating tip across said skin surface.

2. The method of measuring itch sensitivity according to claim 1, wherein said step of contacting a stimulating monofilament comprises repeating said steps of rotating, contacting and dragging each of said plurality of monofilaments individually, one-by-one, sequentially in order of diameter.

3. The method of measuring itch sensitivity according to claim 1, comprising applying said increasing force until said individually operable stimulating monofilament bends at a substantially 45° angle to said skin surface.

4. The method of measuring itch sensitivity according to claim 3, wherein said force is applied to maintain said angle at substantially 45° during said dragging step.

5. The method of measuring itch sensitivity according to claim 1, wherein said dragging step comprises dragging said bent stimulating monofilament across said skin surface both distally and proximally.

* * * * *